US012791987B2

(12) United States Patent
Gureev et al.

(10) Patent No.: US 12,791,987 B2

(45) Date of Patent: Nov. 10, 2026

(54) TECHNIQUES FOR TIME-BASED MEASUREMENTS USING PHOTODETECTORS

(71) Applicant: ActLight SA, Lausanne (CH)

(72) Inventors: Maxim Gureev, St-Sulpice (CH); Lucas Perrin, Gland (CH)

(73) Assignee: ActLight SA, Lausanne (CH)

( * ) Notice: Subject to any disclaimer, the term of this patent is extended or adjusted under 35 U.S.C. 154(b) by 121 days.

(21) Appl. No.: 18/817,119

(22) Filed: Aug. 27, 2024

(65) Prior Publication Data

US 2026/0064082 A1 Mar. 5, 2026

(51) Int. Cl.

*G04F 10/00* (2006.01)
*A61B 5/00* (2006.01)
*A61B 5/024* (2006.01)
*G01N 21/552* (2014.01)
*G06F 1/16* (2006.01)

(52) U.S. Cl.

CPC ......... *G04F 10/005* (2013.01); *G01N 21/552* (2013.01); *G06F 1/163* (2013.01); *A61B 5/02427* (2013.01); *A61B 5/6826* (2013.01)

(58) Field of Classification Search

CPC ..... G04F 10/005; G01N 21/552; G06F 1/163; A61B 5/02427; A61B 5/6826

See application file for complete search history.

(56) References Cited

U.S. PATENT DOCUMENTS 4,202,000 A 5/1980 Carballes
4,484,210 A 11/1984 Shiraki et al.
4,833,346 A 5/1989 Marple
6,808,957 B1 10/2004 Ho et al.
6,992,698 B1 1/2006 Xia
8,569,806 B2 10/2013 Kim
9,012,960 B2 4/2015 Okhonin
9,109,902 B1 * 8/2015 Rulkov ................ A61B 5/6804
9,142,692 B2 9/2015 Sheu (Continued)

FOREIGN PATENT DOCUMENTS

CN 1815744 A 8/2006
CN 101236995 A 8/2008

(Continued)

OTHER PUBLICATIONS

Cova et al., "Avalanche Photodiodes and Quenching Circuits for Single-Photon Detection," Applied Optics, Optical Society of America, Washington, DC, US, vol. 35, No. 12, Apr. 20, 1996, pp. 1956-1976 (21 pages).

(Continued)

*Primary Examiner* — Lam T Mai

(74) *Attorney, Agent, or Firm* — Wilmer Cutler Pickering Hale and Dorr LLP

(57) ABSTRACT

Techniques for time-based measurements using photodetectors are disclosed. In one particular embodiment, the techniques may be realized as a system for determining a physiological parameter comprising one or more photodetector systems configured to receive light from a light source and including a front-end circuit and a photodetector and time-to-digital converter circuitry configured to receive a sensing signal from the front-end circuit and output a triggering time for determining the physiological parameter.

18 Claims, 11 Drawing Sheets

SYSTEM 400

(56) References Cited

U.S. PATENT DOCUMENTS

| | | | | |
|---|---|---|---|---|
| 9,167,975 | B1 * | 10/2015 | Brady | A61B 5/725 |
| 9,236,520 | B2 | 1/2016 | Okhonin et al. | |
| 9,431,566 | B2 | 8/2016 | Okhonin | |
| 9,735,304 | B1 | 8/2017 | Okhonin et al. | |
| 10,204,504 | B1 * | 2/2019 | Lin | G01P 15/18 |
| 10,269,855 | B2 | 4/2019 | Sallin et al. | |
| 10,312,274 | B1 | 6/2019 | Stark | |
| 10,620,591 | B2 * | 4/2020 | Rothkopf | A61B 5/01 |
| 10,687,717 | B1 * | 6/2020 | Peterson | A61B 5/14551 |
| 10,945,648 | B2 | 3/2021 | Poeze et al. | |
| 10,964,837 | B2 | 3/2021 | Sallin et al. | |
| 11,114,480 | B2 | 9/2021 | Okhonin et al. | |
| 11,183,524 | B2 | 11/2021 | Sato | |
| 11,251,217 | B2 | 2/2022 | Okhonin et al. | |
| 11,350,860 | B1 * | 6/2022 | Wong | A61B 5/681 |
| 11,587,960 | B2 | 2/2023 | Okhonin et al. | |
| 11,735,677 | B2 | 8/2023 | Gureev et al. | |
| 12,089,931 | B1 * | 9/2024 | Duan | A61B 5/6844 |
| 2001/0017786 | A1 | 8/2001 | Woodward | |
| 2003/0001080 | A1 | 1/2003 | Kummaraguntla et al. | |
| 2003/0223053 | A1 | 12/2003 | Liu et al. | |
| 2006/0022223 | A1 | 2/2006 | Kumesawa | |
| 2006/0039666 | A1 | 2/2006 | Knights et al. | |
| 2008/0277701 | A1 | 11/2008 | Lee et al. | |
| 2010/0084729 | A1 | 4/2010 | Steinbrueck et al. | |
| 2010/0155806 | A1 | 6/2010 | Fourches | |
| 2010/0230720 | A1 | 9/2010 | Wicks | |
| 2010/0237455 | A1 | 9/2010 | Lee | |
| 2010/0271108 | A1 | 10/2010 | Sanfilippo et al. | |
| 2011/0024808 | A1 | 2/2011 | Janesick | |
| 2011/0133160 | A1 | 6/2011 | Yu et al. | |
| 2011/0220969 | A1 | 9/2011 | Masuoka et al. | |
| 2011/0272561 | A1 | 11/2011 | Sanfilippo et al. | |
| 2011/0292380 | A1 | 12/2011 | Bamji | |
| 2012/0056096 | A1 | 3/2012 | Abeles et al. | |
| 2012/0106971 | A1 * | 5/2012 | Sugaya | H04J 14/0275 398/97 |
| 2012/0287417 | A1 * | 11/2012 | Mimeault | G01S 17/42 356/5.01 |
| 2012/0313155 | A1 | 12/2012 | Okhonin | |
| 2013/0056708 | A1 | 3/2013 | Kim | |
| 2013/0178754 | A1 * | 7/2013 | Rulkov | A61B 5/4866 600/508 |
| 2013/0214355 | A1 | 8/2013 | Fang et al. | |
| 2013/0242314 | A1 | 9/2013 | Fowler et al. | |
| 2013/0278917 | A1 | 10/2013 | Korekado et al. | |
| 2013/0323873 | A1 | 12/2013 | Elasser et al. | |
| 2014/0159188 | A1 | 6/2014 | Maimon | |
| 2014/0210035 | A1 | 7/2014 | Park et al. | |
| 2014/0319640 | A1 | 10/2014 | Major et al. | |
| 2015/0221806 | A1 | 8/2015 | Okhonin | |
| 2016/0317052 | A1 * | 11/2016 | Pan | A61B 5/024 |
| 2017/0019269 | A1 * | 1/2017 | Caffee | H04L 12/423 |
| 2017/0090019 | A1 | 3/2017 | Slobodyanyuk et al. | |
| 2017/0212223 | A1 | 7/2017 | Slobodyanyuk et al. | |
| 2017/0365636 | A1 | 12/2017 | Mazzillo et al. | |
| 2018/0175095 | A1 | 6/2018 | Sallin et al. | |
| 2018/0247968 | A1 | 8/2018 | Na et al. | |
| 2019/0013427 | A1 | 1/2019 | Ting et al. | |
| 2019/0067357 | A1 | 2/2019 | Cheng et al. | |
| 2019/0097075 | A1 | 3/2019 | Rae | |
| 2019/0252570 | A1 | 8/2019 | Sallin et al. | |
| 2019/0257950 | A1 | 8/2019 | Patanwala et al. | |
| 2019/0312170 | A1 | 10/2019 | Roy | |
| 2019/0353760 | A1 | 11/2019 | Hasegawa | |
| 2020/0026031 | A1 | 1/2020 | Li | |
| 2020/0096614 | A1 | 3/2020 | Amaya-Benitez | |
| 2020/0135776 | A1 | 4/2020 | Finkelstein | |
| 2020/0144436 | A1 | 5/2020 | Van Nieuwenhove et al. | |
| 2020/0168649 | A1 | 5/2020 | Ingelberts | |
| 2020/0185560 | A1 | 6/2020 | Giroud-Garampon et al. | |
| 2020/0264291 | A1 * | 8/2020 | Day | G01S 17/10 |
| 2020/0300983 | A1 * | 9/2020 | Morarity | G01S 7/4865 |
| 2020/0323450 | A1 * | 10/2020 | He | A61B 5/0059 |
| 2021/0173353 | A1 * | 6/2021 | Ferri | G06F 3/0482 |
| 2022/0057522 | A1 * | 2/2022 | Mostafanezhad | G01S 17/894 |
| 2023/0210391 | A1 * | 7/2023 | He | A61B 5/0059 600/301 |
| 2023/0228855 | A1 | 7/2023 | Perrin et al. | |
| 2023/0375678 | A1 * | 11/2023 | Cadugan | G01S 7/4863 |
| 2024/0000328 | A1 * | 1/2024 | Kangas | A61B 5/02427 |
| 2024/0237904 | A1 * | 7/2024 | Mäkinen | A61B 5/0205 |
| 2024/0260860 | A1 * | 8/2024 | Mäkinen | A61B 5/14521 |
| 2024/0318985 | A1 * | 9/2024 | Ko | G01D 5/24 |
| 2025/0279834 | A1 * | 9/2025 | Kim | H04L 27/26 |
| 2026/0009901 | A1 * | 1/2026 | Wolfe | G01S 7/4876 |

FOREIGN PATENT DOCUMENTS

| | | | |
|---|---|---|---|
| CN | 102460763 | A | 5/2012 |
| CN | 102891154 | A | 1/2013 |
| CN | 102901992 | A | 1/2013 |
| CN | 103515465 | A | 1/2014 |
| CN | 105849908 | A | 8/2016 |
| CN | 108140656 | A | 6/2018 |
| CN | 109155325 | A | 1/2019 |
| CN | 110416335 | A | 11/2019 |
| EP | 2357669 | A2 | 8/2011 |
| EP | 3570534 | A1 | 11/2019 |
| JP | H05-110056 | A | 4/1993 |
| JP | H07-142761 | A | 6/1995 |
| JP | H07-302928 | A | 11/1995 |
| JP | H08-506456 | A | 7/1996 |
| JP | H09-331051 | | 12/1997 |
| JP | 2003-244074 | A | 8/2003 |
| JP | 2005-235893 | A | 9/2005 |
| JP | 2005-303268 | A | 10/2005 |
| JP | 2005-347599 | A | 12/2005 |
| JP | 2006-210919 | | 8/2006 |
| JP | 2007-526448 | A | 9/2007 |
| JP | 2011-007622 | A | 1/2011 |
| JP | 2013/157619 | A | 8/2013 |
| JP | 2016-066766 | | 4/2016 |
| JP | 2018-088488 | | 6/2018 |
| JP | 2018-190797 | | 11/2018 |
| TW | 446196 | U | 7/2001 |
| WO | WO-2004/114369 | A2 | 12/2004 |
| WO | WO-2005/078801 | | 8/2005 |
| WO | WO-2013/124956 | A1 | 8/2013 |
| WO | WO-2014/021115 | | 2/2014 |
| WO | WO-2018/160721 | A1 | 9/2018 |
| WO | WO-2018/167567 | | 9/2018 |
| WO | WO-2020/212303 | | 10/2020 |
| WO | WO-2020/212305 | | 10/2020 |
| WO | WO-2021/009978 | | 1/2021 |
| WO | WO-2021/009979 | | 1/2021 |
| WO | WO-2022/208167 | A1 | 10/2022 |

OTHER PUBLICATIONS

Fossum, et al., "A Review of the Pinned Photodiode for CCD and CMOS Image Sensors," IEEE Journal of the Electron Devices Society, vol. 2, No. 3, pp. 33-43, May 2014.

Gureev, Maxim et al., "Photodiodes: Dynamic Photodiodes Reach Single-Photon Sensitivity at Low Voltages, with Minimal Noise," Laser Focus World, Feb. 1, 2019 (10 pages).

Ingelberts, H, et al., "A Current-Assisted CMOS Photonic Sampler with Two Taps for Fluorescence Lifetime Sensing," Proceedings of SPIE, vol. 9896, Apr. 29, 2016 (8 pages).

International Search Report and Written Opinion dated Aug. 21, 2018 received in related PCT Application No. PCT/IB2018/000453 filed Apr. 5, 2018 (13 pages).

International Search Report received in International Application No. PCT/IB2021/000497 dated Dec. 22, 2021 (20 pages).

Klein, P., et al., "Design and Performance of Semiconductor Detectors With Integrated Amplification and Charge Storage Capability," Nuclear Instruments & methods in Physics Research. Section A: Accelerators, Spectrometers, Detectors, and Associated Equipment, Elsevier BV, vol. A305, Aug. 1, 1991, pp. 517-526 (10 pages).

Notice of Reasons for Rejection received in related Japanese Patent Application No. 2016-547246. 6 pages.

(56) References Cited

OTHER PUBLICATIONS

Notification of International Search Report and Written Opinion dated Aug. 5, 2022 in related PCT/IB2022/000164 filed Mar. 29, 2022 (11 pages).
Notification of International Search Report and Written Opinion dated Jun. 28, 2018 in related PCT/IB2018/000356 filed Mar. 16, 2018 (19 pages).
Okhonin, et al., "A Dynamic Operation of a PIN photodiode," Applied Physics Letters, American Institute of Physics, vol. 106, No. 3, Jan. 22, 2015 (6 pages).
Raissi, "A brief analysis of the field effect diode and breakdown transistor," IEEE Transactions on Electron Devices, Feb. 1996, vol. 43, Issue 2, pp. 362-365 (4 pages).
Sallin, Denis, et al., " MOS-PN Hybrid Device With Minimum Dark Current for Sensitive Digital Photodetection," IEEE Photonics Technology Letters, IEEE, USA, vol. 26, No. 20, Oct. 15, 2014 pp. 2062-2065. (4 pages).
Salman, et al., "Field Effect Diode (FED): A Novel Device for ESD protection in deep sub-micron SOI technologies," Electron Devices Meeting, 2006, IEDM '06 International, pp. 1-4 (4 pages).
Takahashi, et al., "A 45 nm Stacked CMOS Image Sensor Process Technology for Submicron Pixel," Article, Sensors, MDPI, www.mdpi.com/journal/sensors, pp. 1-13, Basel, Switzerland, Dec. 5, 2017.
Van Nieuwenhove et al., "Photonic Demodulator With Sensitivity Control," IEEE Sensors Journal, IEEE Service Center, vol. 7, No. 3, Mar. 1, 2007, pp. 317-318 (2 pages).

* cited by examiner

SYSTEM 300

SYSTEM 400

SYSTEM 500

TECHNIQUES FOR TIME-BASED MEASUREMENTS USING PHOTODETECTORS

FIELD OF THE DISCLOSURE

The present disclosure relates generally to photodetectors and, more particularly, to techniques for time-based measurements using photodetectors.

BACKGROUND OF THE DISCLOSURE

Photodetectors have been used to detect light that is subsequently reflected off or transmitted through a person's tissue. A photodetector encounters the reflected/transmitted light and produces an electrical signal representative thereof. A current of the electrical signal may increase proportionally to a rate of absorbed photons in the photodetector. Based on this current, a physiological parameter may be derived. However, because the current of the electrical signal is typically weak, an amplifier is often used to boost the magnitude of the electrical signal and derive the physiological parameter therefrom.

The use of an amplifier may cause several drawbacks to a photodetector's performance. For example, circuitry including the amplifier may consume a significant amount of power and may add noise to the electrical signal produced by the photodetector. As such, it may be preferable to avoid using an amplifier with a photodetector.

In view of the foregoing, it is understood that there may be significant problems and shortcomings associated with current photodetector technologies.

SUMMARY OF THE DISCLOSURE

Techniques for time-based measurements using photodetectors are disclosed. A photodetector and a front end may form a photodetector system. In one particular embodiment, the techniques may be realized as a system for determining a physiological parameter, the system comprising one or more photodetector systems configured to receive light from a light source and including a front-end circuit and a photodetector and time-to-digital converter circuitry configured to receive a sensing signal from the front-end circuit and output a triggering time for determining the physiological parameter.

In accordance with other aspects of this particular embodiment, the photodetector may include a cathode and an anode, and the system may further comprise a plurality of switches coupled to the anode and the cathode, wherein the one or more photodetector systems are further configured to produce the sensing signal by operating the plurality of switches to apply a forward bias voltage across the cathode and the anode.

In accordance with further aspects of this particular embodiment, the one or more photodetector systems may be further configured to produce the sensing signal by operating one of the plurality of switches to produce the sensing signal by providing an impedance to the anode, wherein the sensing signal is produced until the impedance transitions to a voltage drop on the anode.

In accordance with additional aspects of this particular embodiment, the impedance may be included in a high impedance mode.

In accordance with other aspects of this particular embodiment, the photodetector may include a gate, the plurality of switches is coupled to the anode, the cathode and the gate, wherein one or more control signals implement a reset mode of operation of the front-end circuit, a load mode of operation of the front-end circuit, and a sense mode of operation of the front-end circuit, wherein the instructions, when executed by the one or more processors, cause the system to put the front-end circuit in the reset mode of operation by connecting the anode to ground, connecting the gate to ground, and applying a reverse bias voltage across the cathode and the anode, put the front-end circuit in the load mode of operation by providing a voltage to the anode and put the front-end circuit in the sense mode by maintaining the anode in a floating state and applying the forward bias voltage across the cathode and the anode.

In accordance with further aspects of this particular embodiment, the system may include one or more processors and memory storing instructions. When executed by the one or more processors, the instructions cause the system to generate a bias signal based on the triggering time, apply the bias signal to the front-end circuit to increase an amount of overlap in time between the sensing signal and another sensing signal of the one or more photodetector systems and determine the physiological parameter responsive to applying the bias signal.

In accordance with additional aspects of this particular embodiment, the instructions, when executed by the one or more processors, may cause the system to apply the bias signal to the front-end circuit to increase the amount of overlap by adjusting an accumulated charge threshold of the photodetector.

In accordance with other aspects of this particular embodiment, the system further may include a plurality of photodetector systems including the one or more photodetector systems, wherein the plurality of photodetector systems and the time-to-digital converter circuitry are included in a group, wherein the system further comprises a plurality of copies of the group, and wherein the instructions, when executed by the one or more processors, cause the system to determine the physiological parameter based on at least one sensing signal from each of the plurality of copies of the group.

In accordance with further aspects of this particular embodiment, the time-to-digital converter circuitry may include at least one counter configured to receive the sensing signal and output the triggering time of the sensing signal.

In accordance with additional aspects of this particular embodiment, the at least one counter may include a plurality of counters connected in series with the front-end circuit of each of the one or more photodetector systems.

In accordance with other aspects of this particular embodiment, the at least one counter may include a plurality of counters connected in parallel to the front-end circuit of each of the one or more photodetector systems.

In accordance with further aspects of this particular embodiment, the physiological parameter may include a heart rate, a blood oxygen level, or a glucose concentration.

In one particular embodiment, the techniques may be realized as a method of controlling one or more photodetector systems to determine a physiological parameter, the method comprising the steps of receiving light provided by a light source at the one or more photodetector systems, the one or more photodetector systems including a front-end circuit and a photodetector that receives the light, producing a sensing signal from the front-end circuit based on the photodetector receiving the light and receiving the sensing signal by time-to-digital converter circuitry that outputs a triggering time for determining the physiological parameter.

In accordance with other aspects of this particular embodiment, the photodetector may include a cathode and an anode, a plurality of switches is coupled to the anode and the cathode, and the method further comprises producing the sensing signal by operating the plurality of switches to apply a forward bias voltage across the cathode and the anode.

In accordance with further aspects of this particular embodiment, the sensing signal may be produced by providing an impedance to the anode, wherein the sensing signal is produced until the impedance transitions to a voltage drop on the anode.

In accordance with additional aspects of this particular embodiment, the photodetector may include a gate, the plurality of switches is coupled to the anode, the cathode and the gate, the method further comprising putting the front-end circuit in a reset mode of operation by connecting the anode to ground, connecting the gate to ground, and applying a reverse bias voltage across the cathode and the anode, putting the front-end circuit in a load mode of operation by providing a voltage to the anode and putting the front-end circuit in a sense mode by maintaining the anode in a floating state and applying the forward bias voltage across the cathode and the anode.

In accordance with other aspects of this particular embodiment, the method may include generating a bias signal based on the triggering time, applying the bias signal to the front-end circuit to increase an amount of overlap in time between the sensing signal and another sensing signal of the one or more photodetector systems and determining the physiological parameter responsive to applying the bias signal.

In accordance with further aspects of this particular embodiment, applying the bias signal may include applying the bias signal to the front-end circuit to increase the amount of overlap by adjusting an accumulated charge threshold of the photodetector.

In accordance with additional aspects of this particular embodiment, the method may include providing a plurality of photodetector systems as a group including the one or more photodetector systems and the time-to-digital converter circuitry, providing a plurality of copies of the group, and the method further comprising determining the physiological parameter based on at least one sensing signal from each of the plurality of copies of the group.

In accordance with other aspects of this particular embodiment, the time-to-digital converter circuitry may include at least one counter and the method further comprises the at least one counter receiving the sensing signal and outputting the triggering time of the sensing signal.

In one particular embodiment, the techniques may be realized as one or more non-transitory computer-readable media storing executable instructions that, when executed by one or more processors, determine a physiological parameter using one or more photodetector systems by receiving light provided by a light source at the one or more photodetector systems, the one or more photodetector systems including a front-end circuit and a photodetector that receives the light, producing a sensing signal from the front-end circuit based on the photodetector receiving the light and receiving the sensing signal by time-to-digital converter circuitry that outputs a triggering time for determining the physiological parameter.

In accordance with further aspects of this particular embodiment, the physiological parameter may include determining a heart rate, a blood oxygen level, or a glucose concentration.

In one particular embodiment, the techniques may be realized as a user-worn device comprising the system.

In accordance with additional aspects of this particular embodiment, the user-worn device may be configured to non-invasively measure a blood oxygen saturation of a user.

In accordance with other aspects of this particular embodiment, the user-worn device further may include a plurality of light emitters.

In accordance with further aspects of this particular embodiment, the user-worn device may include a protrusion comprising a convex surface including the separate openings extending through the protrusion and lined with opaque materials, each opening positioned over a photodetector or light source, the opaque material configured to reduce an amount of light reaching the photodetector without being attenuated by the tissue.

In accordance with additional aspects of this particular embodiment, the user-worn device may include a temperature sensor.

In accordance with other aspects of this particular embodiment, the one or more processors may be configured to receive a temperature signal from the temperature sensor and adjust operation of the user-worn device responsive to the temperature signal.

In accordance with further aspects of this particular embodiment, the plurality of emitters may include at least one emitter configured to emit light on first wavelength, and a second emitter configured to emit light on the second wavelength.

In one particular embodiment, the techniques may be realized as a system for determining a health measurement, the system comprising a plurality of photodetectors configured to receive light from a light source, wherein each photodetector of the plurality of photodetectors includes a photodetector and a front-end circuit, time-to-digital converter circuitry configured to receive a sensing signal from the front-end circuit and output a triggering time, and one or more processors. The system also includes memory storing instructions that, when executed by the one or more processors, cause the system to: generate a bias signal based on the triggering time, apply the bias signal to the front-end circuit to increase an amount of overlap in time between the sensing signals of at least two of the plurality of photodetectors, and determine the health measurement responsive to applying the bias signal.

In accordance with other aspects of this particular embodiment, the front-end circuit may include a plurality of switches connected to a gate, a cathode, and an anode of the photodetector, and the instructions, when executed by the one or more processors, may cause the system to: provide one or more control signals to the front-end circuit to operate the plurality of switches, apply a forward bias voltage across the cathode and the anode of the photodetector to produce the sensing signal, and apply the bias signal to the gate to increase the amount of overlap.

In accordance with further aspects of this particular embodiment, the sensing signal may begin responsive to the front-end circuit applying the forward bias and may end responsive to a voltage drop on the anode.

In accordance with additional aspects of this particular embodiment, the one or more control signals may implement a reset mode of operation, a load mode of operation, and a sense mode of operation, wherein the instructions, when executed by the one or more processors, may cause the system to put the front-end circuit in the reset mode of operation by connecting the anode to ground, connecting the gate to ground, and applying a reverse bias voltage across the cathode and the anode, put the front-end circuit in the load mode of operation by providing a voltage to the anode, put the front-end circuit in the sense mode by maintaining the anode in a floating state and applying the forward bias voltage across the cathode and the anode.

In accordance with other aspects of this particular embodiment, the front-end circuit does not include an amplifier.

In accordance with further aspects of this particular embodiment, the time-to-digital converter circuitry does not include an amplifier.

In accordance with additional aspects of this particular embodiment, the time-to-digital converter circuitry may include at least one counter configured to receive the sensing signal and output the triggering time of the sensing signal.

In accordance with other aspects of this particular embodiment, the instructions, when executed by the one or more processors, may cause the system to generate the bias signal based on the triggering time of the sensing signal output by the at least one counter and apply the bias signal to the photodetector to increase the amount of overlap by adjusting an accumulated charge threshold of the photodetector having a longest triggering time.

In accordance with further aspects of this particular embodiment, the at least one counter may include a plurality of counters connected in series with the front-end circuit of each of the one or more photodetector systems.

In accordance with additional aspects of this particular embodiment, the at least one counter may include a plurality of counters connected in parallel to the front-end circuit of each of the one or more photodetector systems.

In accordance with other aspects of this particular embodiment, the plurality of photodetectors and the time-to-digital converter circuitry may be included in a group, wherein the system may include a plurality of copies of the group, and wherein the instructions, when executed by the one or more processors, may cause the system to determine the health measurement based on the sensing signal from each of the plurality of copies of the group.

In accordance with further aspects of this particular embodiment, determining the health measurement may include determining a heart rate, a blood oxygen level, or a glucose concentration.

In one particular embodiment, the techniques may be realized as a method of controlling a system of photodetectors to determine a health measurement. The method may comprise the steps of: receiving light provided by a light source at a plurality of photodetectors, each photodetector of the plurality of photodetectors including a photodetector and a front-end circuit, receiving a sensing signal from the front-end circuit at time-to-digital converter circuitry, outputting a triggering time from the time-to-digital converter circuitry, generating a bias signal based on the triggering time, applying the bias signal to the front-end circuit to increase an amount of overlap in time between the sensing signals of at least two of the plurality of photodetectors, and determining the health measurement responsive to applying the bias signal.

In accordance with other aspects of this particular embodiment, the front-end circuit may include a plurality of switches connected to a gate, a cathode, and an anode of the photodetector, and the method may comprise the steps of providing one or more control signals to the front-end circuit to operate the plurality of switches, applying a forward bias voltage across the cathode and the anode of the photodetector to produce the sensing signal, and applying the bias signal to the gate to increase the amount of overlap.

In accordance with further aspects of this particular embodiment, the one or more control signals may implement a reset mode of operation, a load mode of operation, and a sense mode of operation, and the method may comprise the steps of: putting the front-end circuit in the reset mode of operation by connecting the anode to ground, connecting the gate to ground, and applying a reverse bias voltage across the cathode and the anode, putting the front-end circuit in the load mode of operation by providing a voltage to the anode, putting the front-end circuit in the sense mode by maintaining the anode in a floating state and applying the forward bias voltage across the cathode and the anode.

In accordance with additional aspects of this particular embodiment, the front-end circuit does not include an amplifier and receiving the sensing signal may comprise receiving the sensing signal without using an amplifier.

In accordance with other aspects of this particular embodiment, the time-to-digital converter circuitry does not include an amplifier and outputting the outputting the triggering time from the time-to-digital converter circuitry may comprise outputting the triggering time without using an amplifier.

In accordance with further aspects of this particular embodiment, determining the health measurement may include determining a heart rate, a blood oxygen level, or a glucose concentration.

In one particular embodiment, the techniques may be realized as one or more non-transitory computer-readable media storing executable instructions that, when executed by one or more processors, cause a system to determine a health measurement by receiving light provided by a light source at a plurality of photodetectors, wherein each photodetector of the plurality of photodetectors includes a photodetector and a front-end circuit, receiving a sensing signal from the front-end circuit at time-to-digital converter circuitry, outputting a triggering time from the time-to-digital converter circuitry, generating a bias signal based on the triggering time, applying the bias signal to the front-end circuit to increase an amount of overlap in time between the sensing signals of at least two of the plurality of photodetectors, and determining the health measurement responsive to applying the bias signal.

In accordance with other aspects of this particular embodiment, determining the health measurement may include determining a heart rate, a blood oxygen level, or a glucose concentration.

In one particular embodiment, the techniques may be realized as at least one processor readable storage medium storing a computer program of instructions configured to be readable by at least one processor for instructing the at least one processor to execute a computer process for performing the method.

In one particular embodiment, the techniques may be realized as a non-transitory computer readable medium storing a computer program of instructions configured to be executed by one or more processors of the system to execute a computer process for performing the method.

In another embodiment, the front-end circuit does not include any amplifier.

In one embodiment, the time-to-digital converter circuitry does not include any amplifier.

In accordance with further aspects of this particular embodiment, the photodetector is a dynamic photodetector.

The present disclosure will now be described in more detail with reference to particular embodiments thereof as shown in the accompanying drawings. While the present disclosure is described below with reference to particular embodiments, it should be understood that the present disclosure is not limited thereto. Those of ordinary skill in the art having access to the teachings herein will recognize additional implementations, modifications, and embodiments, as well as other fields of use, which are within the scope of the present disclosure as described herein, and with respect to which the present disclosure may be of significant utility.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be illustrative only.

DETAILED DESCRIPTION OF EMBODIMENTS

In the following detailed description, for purposes of explanation and not limitation, specific details are set forth in order to provide a better understanding of the present disclosure. It will be apparent to one skilled in the art that the present disclosure may be practiced in other embodiments that depart from these specific details.

Semiconductor photodiodes are a common type of photodetector. In general, a traditional photodiode operates by receiving optical energy and converting that energy into an electric current. The traditional photodiode contains two strongly p- and n-doped regions separated by a weakly doped (or undoped) region and is kept at a fixed reverse bias voltage. Under illumination, the current produced by the photodiode increases proportionally to the rate of absorbed photons. However, because this current is very small, amplifiers (e.g., transimpedance amplifiers) are used to boost the signal so that it may be adequately processed. Typically, these amplifiers are included in the front end of a photodetector.

Using an amplifier in a front end or a front-end circuit can increase overall physical die/chip area, consume significant amounts of power, and/or introduce noise into the signal being measured. While one approach is to model the amplifier noise in an attempt to adjust the front end and mitigate negative effects of the amplifier on the measured signal, a better solution is described herein that eliminates the need for the amplifier.

The present disclosure relates to non-invasive methods, devices, and systems for measuring physiological parameters including a heart rate, a blood oxygen level, and various blood constituents or analytes, such as a glucose concentration. Embodiments herein include photodetector systems that do not use an amplifier to boost the signal produced by a photodiode (i.e., unlike a traditional photodiode). Photodetector systems described herein are capable of recovering a usable signal of the same quality (e.g., signal-to-noise ratio (SNR)) as a traditional photodetector, but by using less input light and without adding noise.

Figure 1:
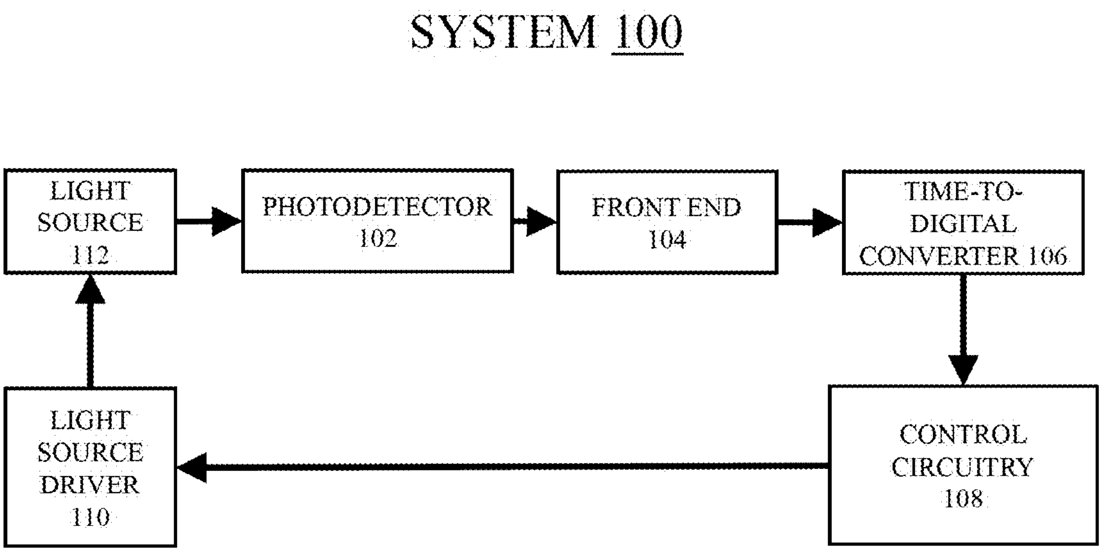
FIG. 1 shows a system including a photodetector, front end, and time-to-digital converter in accordance with an embodiment of the present disclosure.

FIG. 1 shows a measurement system 100 including one or more photodetectors 102, one or more front-end circuits 104, one or more time-to-digital converters 106, control circuitry 108, a light source driver 110, and one or more light sources 112. The arrows in FIG. 1 describe a general processing flow, but it is understood that other connections and directions of processing are possible. Photodetectors of embodiments described herein, including the photodetector 102, in at least one example, may be a photodetector as described in U.S. patent application Ser. No. 16/933,159, entitled "Photodetectors and Photodetector Arrays," filed Jul. 20, 2020 (the '159 application) or a photodetector as described in U.S. patent application Ser. No. 17/580,052, entitled "Control techniques for photodetector systems," filed on Jan. 20, 2022 (the '052 application), which are herein incorporated by reference in their entirety. The photodetector 102 is, in at least one embodiment, a combination of a photodetector as described in the '052 application and a photodetector as described in the '159 application. The photodetector 102 may be a dynamic photodetector.

One or more optical elements (e.g., filters, lenses) can optionally be added between the light source 112 and the photodetector 102. The one or more light sources 112 are configured to output one or more wavelengths of light and/or are individually controllable by the control circuitry 108. The one more optical elements may enhance, alter, or diminish certain properties of the light. In an example, the one or more optical elements include a filter that blocks wavelengths of a certain wavelength or range of wavelengths.

The photodetector 102, in at least one embodiment, differs from a traditional photodiode (e.g., a PIN diode), which operates at a fixed reverse (negative) bias voltage and outputs a weak analog current signal that is proportional to the rate of absorbed of photons within the photodetector. The weak signal needs to be boosted by an amplifier in order to be adequately processed. Embodiments described herein utilize dynamic photodetectors and photodetector systems (e.g., a system including a photodetector and a front end) that operate on a different principle compared to traditional photodiodes. Where a traditional photodiode in a photodetector is used to measure the current produced by a photodiode therein, a dynamic photodetector (DPD) in a photodetector system, in at least certain examples, may be used to measure time (e.g., a start-stop signal, an interval of a signal being a logical 'high'/1 and bookended by the signal being a logical 'no'/0).

The photodetector 102 is, in at least one embodiment, a dynamic photodetector (DPD) that operates under illumination by accumulating a certain critical charge before triggering a strong forward current to flow. The photodetector 102 operates by applying a bias voltage step. The applied bias induces a large output current after a time delay. The time delay is represented as a start-stop signal or a signal having a non-zero value for an interval of time. The time delay is a function of the absorbed light power. Because of the large amplitude of the output of the photodetector 102, the photodetector 102 may be directly integrated with digital circuits without analog amplification and thereby not adding noise.

The front-end circuit 104 is an electrical circuit that controls the photodetector 102 and senses the output of the photodetector 102, which it provides to the time-to-digital converter 106. The time-to-digital converter (TDC) 106 is an electronic device including electrical circuitry that measures a time interval of a signal produced by the photodetector 102 and converts the time interval into a digital representation of the time interval. This digital representation may correspond to a triggering time of the photodetector 102. The triggering time is provided to the control circuitry 108 by the TDC 106. The output of the front-end circuit 104 may correspond to the onset of light encountering the photodetector 102 and an output current being triggered therein.

The control circuitry 108 may include one or more processors that execute instructions stored in a memory and control one or more components of the measurement system 100. In some examples, the control circuitry 108 controls the front-end circuit 104 and/or the light source driver 110. Accordingly, the measurement system 100 is able to precisely coordinate the timing of the light source 112 emitting light and preparing the photodetector 102 to receive the light from a medium (e.g., biological tissue), and adjust the front-end circuit 104 based on a triggering time output by the TDC 106.

Figure 2:
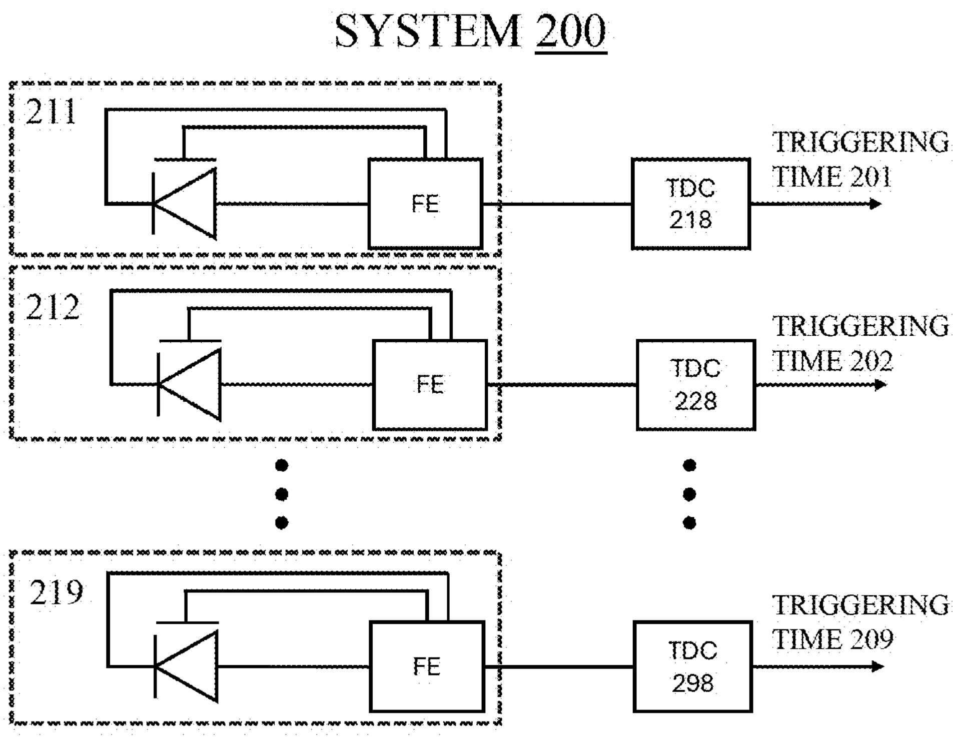
FIG. 2 shows a measurement system with individual time-to-digital converters in accordance with an embodiment of the present disclosure.

Certain applications may include a photodetector system comprised of multiple photodetectors and/or multiple photodetector systems that each include one or more photodetectors. FIG. 2 shows a measurement system 200 that outputs a plurality of triggering times including a first triggering time 201 of a first photodetector system 211, a second triggering time 202 of a second photodetector system 212, and third triggering time 209 of third photodetector system 219. The measurement system 200 includes 3 or more photodetector systems, including the first photodetector system 211 in parallel with the second photodetector system 212 and the third photodetector system 219.

The measurement system 200 outputs a plurality of triggering times including the first triggering time 201 produced by a first TDC 218 coupled to the first photodetector system 211, the second triggering time 202 produced by a second TDC 228 coupled to the second photodetector system 212, and a third triggering time 209 produced by a third TDC 298 coupled to the third photodetector system 219. In some examples, the first TDC 218, the second TDC 228, and third TDC 298 are identical in structure and individually tunable or adjustable. Each triggering time produced by a measurement system may itself be produced by a respective set of a photodetector (e.g., the photodetector 102), a front-end circuit (e.g., the front-end circuit 104), and a TDC (e.g., the TDC 106).

Several photodetector systems can be used in parallel to receive light at substantially the same time, where each photodetector system has its own front end, for example in the manner shown in FIG. 2 as a first photodetector system 211 in parallel with a second photodetector system 212 and third photodetector system 219. The first photodetector system 211 outputs a signal to the first TDC 218, which produces the triggering time 201. Similarly, the second photodetector system 212 and the third photodetector system 219 respectively output signals to the second TDC 228 and the third TDC 298, which in turn produce the second triggering time 202 and third triggering time 209 respectively.

Each detector front end of each photodetector system may be configured separately by the control circuitry 108 to optimize its performance (e.g., adjusting its triggering time). For example, if one detector receives less light compared to others, its sensitivity can be increased (i.e., a lower charge required for triggering) to make its triggering time similar to the others. This may enable a reduction in power consumption relative to a system without adjustment.

Figure 3:
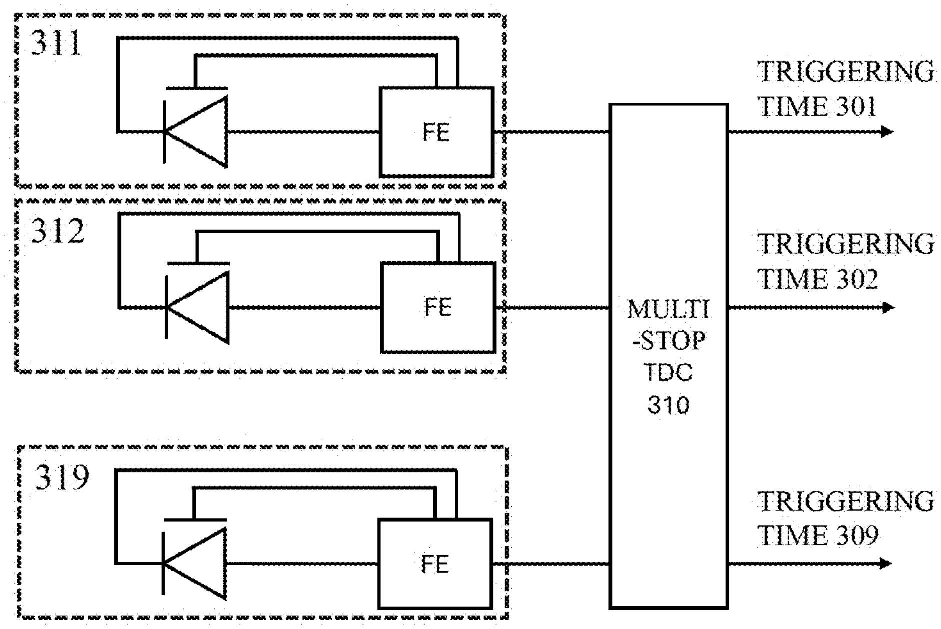
FIG. 3 shows a measurement system and a time-to-digital converter in accordance with an embodiment of the present disclosure.

FIG. 3 shows a measurement system 300 that outputs a plurality of triggering times including a first triggering time 301 of a first photodetector system 311, a second triggering time 302 of a second photodetector system 312, and third triggering time 309 of third photodetector system 319. The measurement system 300 includes 3 or more photodetector systems, including the first photodetector system 311 in parallel with the second photodetector system 312 and the third photodetector system 319. The first photodetector system 311 outputs a signal to a multi-stop TDC 310, which produces the first triggering time 301. Similarly, the second photodetector system 312 and the third photodetector system 319 respectively output signals to the multi-stop TDC 310, which in turn produces the second triggering time 302 and the third triggering time 309.

The measurement system 300 is similar to the measurement system 200. For example, the triggering times 301, 302, 309 of the measurement system 300 may be identical to the triggering times 201, 202, 209 of the measurement system 200. One difference between these two systems is the use of individual TDCs in the measurement system 200 and a single multi-stop TDC 310 in the measurement system 300. Choosing one type of TDC implementation over another may be informed by the number of photodetectors, chip area, power limitations, signal resolution, and so forth for a particular use case.

Figure 4:
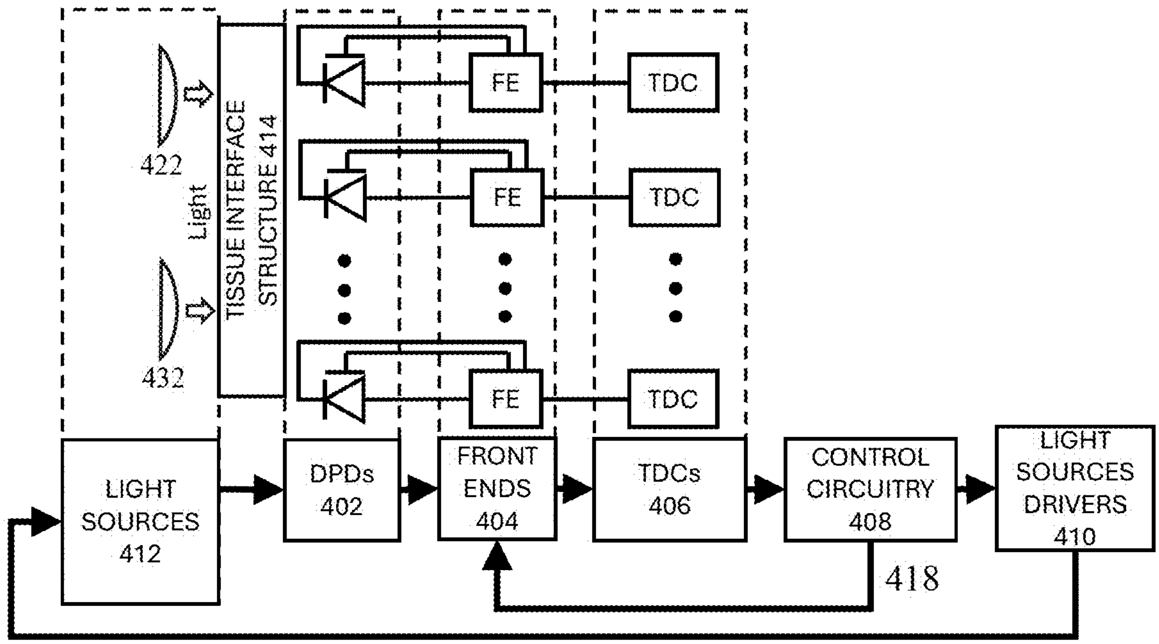
FIG. 4 shows a front end of a photodetector system being tuned in accordance with an embodiment of the present disclosure.

An example measurement system 400 shown in FIG. 4 includes a plurality of light sources 412 that are configured to provide light at one or more wavelengths. Certain wavelengths may be utilized to obtain particular physiological parameters. To measure heart rate, for example, the one or more wavelengths includes 530 nm. The system 400 includes a plurality of DPDs 402, a plurality front ends 404, a plurality TDCs 406, control circuitry 408, and a plurality of light sources drivers 410. The light sources 412 include a first light source 422 driven by one of the light sources drivers 410 to emit light at a first wavelength and a second light source 432 driven by another of the light sources drivers 410 to emit light of a second wavelength.

The measurement system 400 includes a tissue interface structure 414 positioned between the path of emitted light from the first light source 422 and the second light source 432. The tissue interface structure 414 may include a protrusion, surface, or other physical structure shaped to conform to a part of biological tissue. For example, the tissue interface structure 414 may include a transparent or semitransparent material that comes into contact with a part of a body (e.g., the pad of a person's finger) such that the light emitted by the light sources 412 encounters the finger. Some of the light penetrates the skin and reflects off biological structures such as veins and arteries of the finger, whereby the reflected light encounters the DPDs 402, which each have a certain level of accumulated charge that when reached, will trigger a large output current in the respective DPD, which then outputs a signal to the respective TDC 406. Variations of the measurement system 400 are contemplated herein. For example, instead of the individual TDCs 406 as shown in FIG. 4, a single TDC may be used similar to the Multi-Stop TDC 310.

The measurement system 400 may be included in a user-worn device (e.g., smart watch, mobile medical device) having a protrusion shaped by a convex surface to contact a portion of the user's tissue, the convex surface including separate openings extending through the protrusion and lined with opaque materials, each opening positioned over a photodetector (e.g., DPD 402) or light source (e.g., light sources 412), the opaque material configured to reduce an amount of light reaching the photodetector without being attenuated by the tissue.

Measurement systems (e.g., the measurement system 400) may include one or more temperature sensors (e.g., thermistor). A temperature sensor may be placed on or near a light source (e.g., light source 412), electrical component (e.g., front end 404), or tissue interface (e.g., tissue interface structure 414). The temperature sensor may provide a signal to one or more processors or other control circuitry that indicates a certain temperature, upon which the processor may act to tune or adjust the system to maintain performance. In an example, placing one or more temperature sensors near the tissue interface structure 414 enables a determination of a temperature of a person's finger, which in turn may be used to prevent measuring physiological parameters outside of a range of device operating temperatures that would have decreased accuracy and reliability (e.g., too cold). In another example, the one or more processors are configured to receive a temperature signal from the temperature sensor located in a user-worn device and adjust operation of the user-worn device responsive to the temperature signal (e.g., the device is too hot after being left out in the sun). The temperature may be used to tune the photodetectors, for example by adjusting an accumulated charge threshold of a photodetector based on the temperature.

The control circuitry 408 outputs a control signal 418 to one or more of the front ends 404. The control signal 418 is, in some examples, a bias signal. The bias signal includes, for certain examples, a bias voltage that when applied to a DPD, alters (i.e., lowers or raises) a critical charge threshold of the DPD to correspondingly change the triggering time of the DPD.

Figure 5:
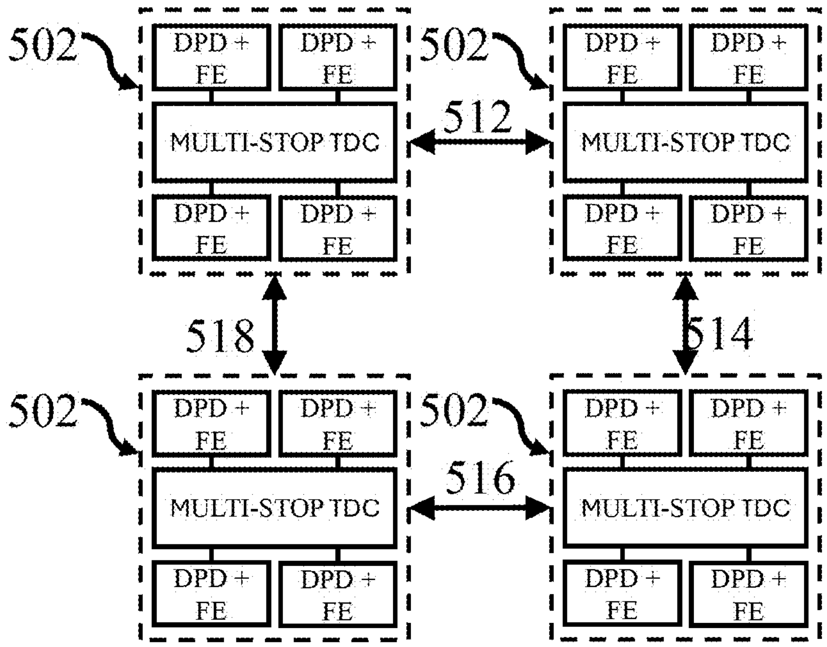
FIG. 5 shows groups of photodetector systems in accordance with an embodiment of the present disclosure.

FIG. 5 shows a measurement system 500 including a plurality of photodetector system groups 502, where each of the photodetector system groups 502 has an identical structure (i.e., copies of one another). Each of the groups 502 includes a multi-stop TDC (e.g., the multi-stop TDC 310) and four individual detectors (i.e., one DPD and one front end per detector). It is understood that each photodetector system may include additional or fewer photodetector systems and each of the groups 502 may include more than four or fewer than four total photodetector systems therein. By grouping photodetector systems in this manner, the measurement system 500 may achieve greater resolution of the measurement signal and any characteristics of this signal used to determine physiological parameters. Physiological parameters may include vital signs and health metrics (e.g., blood oxygen saturation level).

The physiological parameter determination includes analyzing the electrical signal output by a photodetector, a front end, and/or a TDC as described herein. In an example, one or more DPDs are used in combination with two light sources (e.g., the first light source 422 and the second light source 432) of different wavelengths (e.g., 660 nm, 940 nm) that are driven to illuminate in an alternating sequence to derive a pulse oximetry measurement from the electrical signal(s) obtained from the DPDs. The pulse oximetry measurement is one example of a blood oxygen level measurement (e.g., SpO2 percentage). Other physiological parameters that are derived from the signal(s) include a heart rate (e.g., beats per minute (bpm)) and a glucose concentration (e.g., millimoles per liter (mmol/L), milligrams per deciliter (mg/dl)).

Each of the photodetector system groups 502 may be used to calculate, for example, and average triggering time of the DPDs making up the individual photodetector system group 502. In the measurement system 500, for example, an average measurement of one photodetector system group 502 is obtained by computing a measurement (e.g., heart rate) for each of the four detectors in the photodetector system group 502, and then dividing the value of the measurement by 4. In form factors including user-worn devices (e.g., a smart watch), systems described herein (e.g., the measurement systems 200, 300, and 400) facilitate accurate measurements of physiological parameters while being easy-to-user for users thereof.

In a single detector scenario, ensuring maximum overlap between the transmitted light and the sensing signal output by the front-end circuitry is generally less of a concern compared to the multiple detector scenario because there is only one sensor to synchronize with the light source and not multiple sensors at different distance from each other and the light source(s). With a single detector, after the photodetector is triggered, the light source is switched off to avoid unnecessary power consumption. Turning off the power as close in time as possible after or with the triggering is unlike the multi-detector scenario which makes turning off the light source at an optimal time more of a challenge. This challenge is exemplified in more detail in the discussion of FIG. 9.

FIG. 5 shows a plurality of distances between each of the photodetector system groups 502, which may be physically coupled to a substrate that keeps their relative positions fixed. A first distance 512 of these distances is a three-dimensional distance between a first pair of the four photodetector system groups 502. A second distance 514 is a three-dimensional distance between a second pair of the photodetector system groups 502. A third distance 516 is a three-dimensional distance between a third pair of the photodetector system groups 502. A fourth distance 518 is a three-dimensional distance between the remaining pair of the 4 photodetector system groups 502 of the measurement system 500. The reference points of each distance may be a common point relative to each of the photodetector systems (e.g., a center of mass, center of a common external side).

The photodetector system groups 502 may be arranged in a symmetrical or asymmetrical pattern. As an example of a symmetrical pattern, the first distance 512, the second instance 514, the third distance 516, and the fourth distance 518 are equivalent. As an example of an asymmetrical pattern, the photodetector system groups 502 are arranged in a sequence along a line, one after the other, where at least one of the first distance 512, the second instance 514, the third distance 516, and the fourth distance 518 is not the same as the others.

One benefit of the photodetector systems described herein is an ability to fine tune the accumulated charge threshold of each photodetector individually. In systems that employ multiple photodetectors, for example the measurement system 500, incoming light may reach each of the photodetector systems 502 at a different time or with a different intensity causing one photodetector to have a longer trigger time than any of the other photodetectors. Accordingly, the triggering time derived by the TDC of the respective photodetector system 502 may be used to adjust the accumulated charge thresholds to thereby make each signal produced by a front end thereof (e.g., a sensing signal) overlap as much as possible. The triggering time of the last photodetector to trigger may form a basis for adjusting the critical charge thresholds of any photodetector in the system.

To make triggering times of photodetectors more similar to one another, in at least some examples, a sensitivity of a photodetector is adjusted to make its corresponding triggering time be more similar to another photodetector. This may enable an optimal signal while keeping power consumption low. If one sensor triggered, and another sensor continues measurement, the light source will be on. The light coming to the first sensor will be wasted.

Figure 6A:
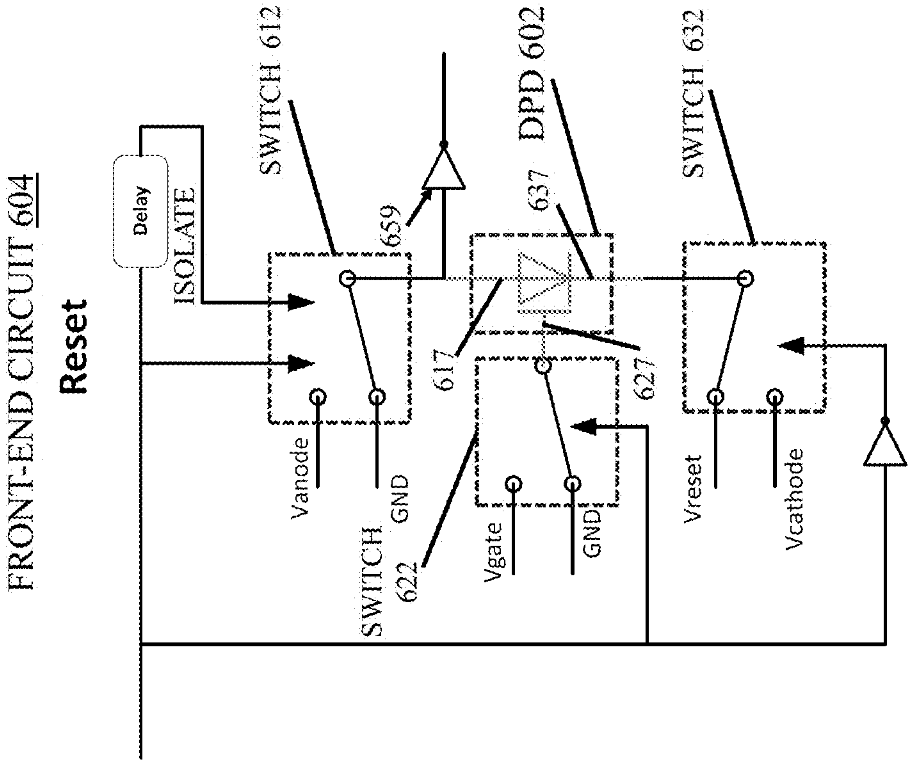
FIG. 6A shows a front-end circuit in a reset mode in accordance with an embodiment of the present disclosure.
Figure 6B:
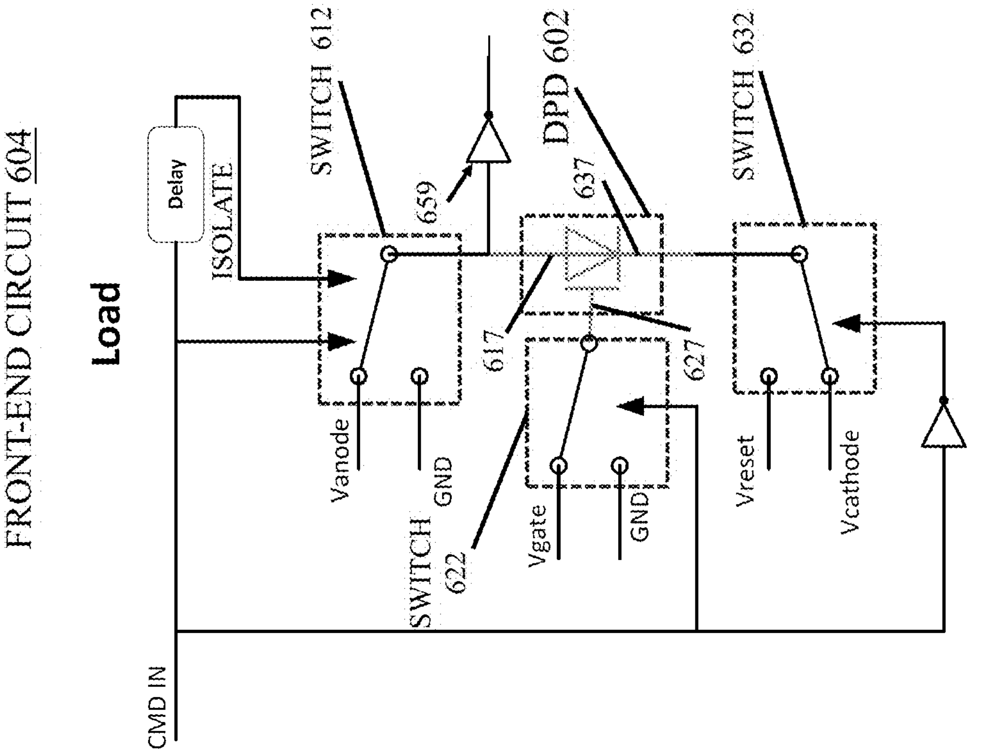
FIG. 6B shows a front-end circuit in a load mode in accordance with an embodiment of the present disclosure.
Figure 6C:
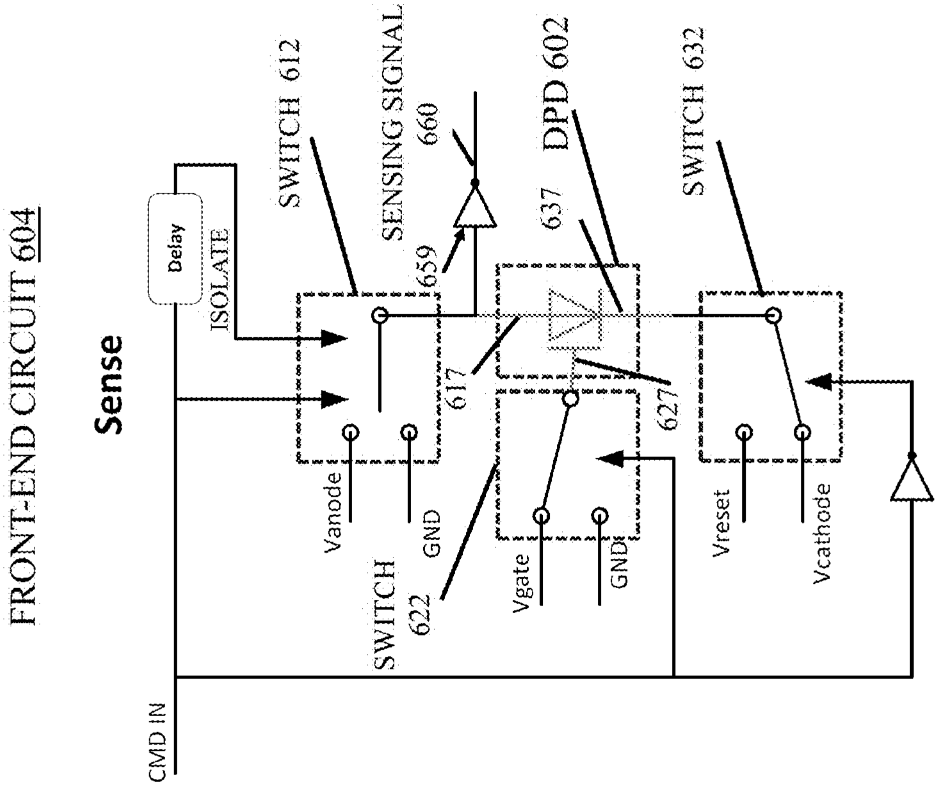
FIG. 6C shows a front-end circuit in a sense mode in accordance with an embodiment of the present disclosure.

Front end circuits as described herein may achieve an overall reduction in power consumption without adding noise (as compared to systems that use amplifiers). A front-end circuit 604 including a DPD 602 is shown in FIGS. 6A, 6B, and 6C. The DPD 602 provides a sensing signal 660 to a TDC (e.g., the TDC 106). FIG. 6A shows the front-end circuit 604 in a Reset mode of operation. The front-end circuit 604 may include a plurality of switches including a first switch 612, a second switch 622, and a third switch 632. The first switch 612 is configured to receive one or more control signals (e.g., from the control circuitry 108) and provide a connection between an anode 617 of the DPD 602 and Vanode (anode voltage) or GND (ground). The second switch 622 is configured to receive one or more control signals and provide a connection between a gate 627 of the DPD 602 and Vgate (gate voltage) or GND. The third switch 632 is configured to receive one or more control signals and provide a connection between a cathode 637 of the DPD 602 and Vreset (reset voltage) and Vcathode (cathode voltage). FIG. 6B shows the front-end circuit 604 in a Load mode of operation. FIG. 6C shows the front-end circuit 604 in a Sense mode of operation.

In the Reset mode of operation, a reverse bias voltage is applied to DPD 602 and the gate 627 of the DPD 602 is connected to ground (GND). In the Load mode of operation, the cathode 637 of the DPD 602 is connected to a cathode voltage (Vcathode) and the gate 627 is connected to gate voltage (Vgate). Also in the Load mode of operation, the anode 617 of the DPD 602 is preloaded to Vanode. During the Load mode of operation, Vanode is, in at least one example, 1 Volt. In the Sense mode of operation, the anode stays floating and a forward bias is applied to the DPD 602. As soon as the forward current starts to increase in the DPD 602, voltage on the anode node drops and the DPD 602 gives an output signal (e.g., the sensing signal 660) corresponding to the triggering time of the DPD 602. The output signal is provided through a NOT gate 659.

The increase in current may be produced without a cathode in certain embodiments. In an example, the current flows between contacts of the same type (i.e., no forward bias) and charging the barrier (e.g., created by a gate) leads to the current increase. Certain embodiments may include a DPD without a gate (e.g., a photodetector described in the '159 application).

The front-end circuit 604 receives a control signal CMD_IN from an external peripheral (e.g., a microcontroller). A delayed signal ISOLATE is generated in the front-end circuit 604 to control the tri-state switch on the anode side of the DPD 602 (i.e., the first switch 612). The ISOLATE signal puts the anode 617 in a high impedance mode during the Sense mode of operation. The high impedance mode may permit little to no current at the anode 617 such that the NOT gate 659 outputs a logical 'high'/1 during the Sense mode until a voltage drop on the anode 617, upon which the NOT gate 659 outputs a logical 'low'/0.

Figure 7:
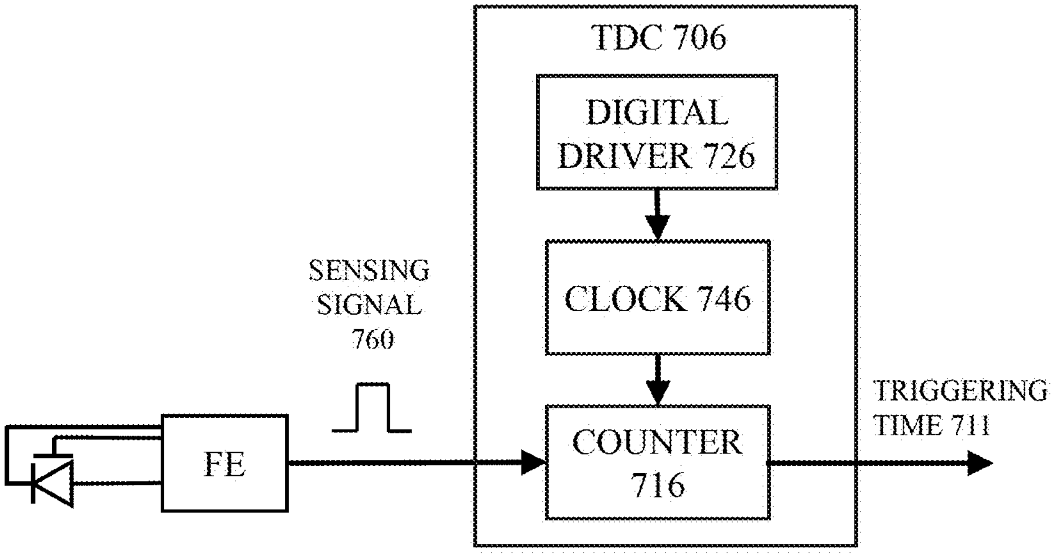
FIG. 7 shows a time-to-digital converter that outputs a triggering time in accordance with an embodiment of the present disclosure.

FIG. 7 shows a TDC 706 including a digital driver 726, a clock 746, and a counter 716. Upon triggering of a photodetector in a photodetector system, a front-end circuit of the photodetector system provides a sensing signal 760 to the counter 716. The digital driver 706 controls the clock 746 and the counter 716. In an example, the digital driver 706 enables the clock 746 and resets the counter 716 for a new measurement. The clock 746 may comprise a single clock, for example in a microcontroller, or more clocks running at different speeds to enhance time resolution. The counter 716 may be a register in a microcontroller, or many counters counting the cycle of different clocks 746 or storing the state of one or different clocks 746.

The sensing signal 760, in some examples, is a start-stop signal, indicating the start of charge accumulation in a photodetector and the triggering of the forward current in the photodetector. By counting how many clock cycles occurred between a start of the sensing signal 760 and an end of the sensing signal 760, for example, the TDC 706 provides a triggering time 711. The triggering time 711 represents an amount of time (as opposed to an electrical current) before the sensing signal 760 changed states (e.g., from high to low). The counter 716, in some examples, is a digital counter that provides a value (i.e., triggering time 711) that is proportional to the actual triggering time of the corresponding DPD that triggered the sensing signal 760 to change states. The counter 716, in some examples, can be modified to change a resolution of the counting, for example to either a coarse counting or a fine counting, thereby providing an adjustable parameter to balance battery life against signal resolution or sampling frequency.

Figure 8:
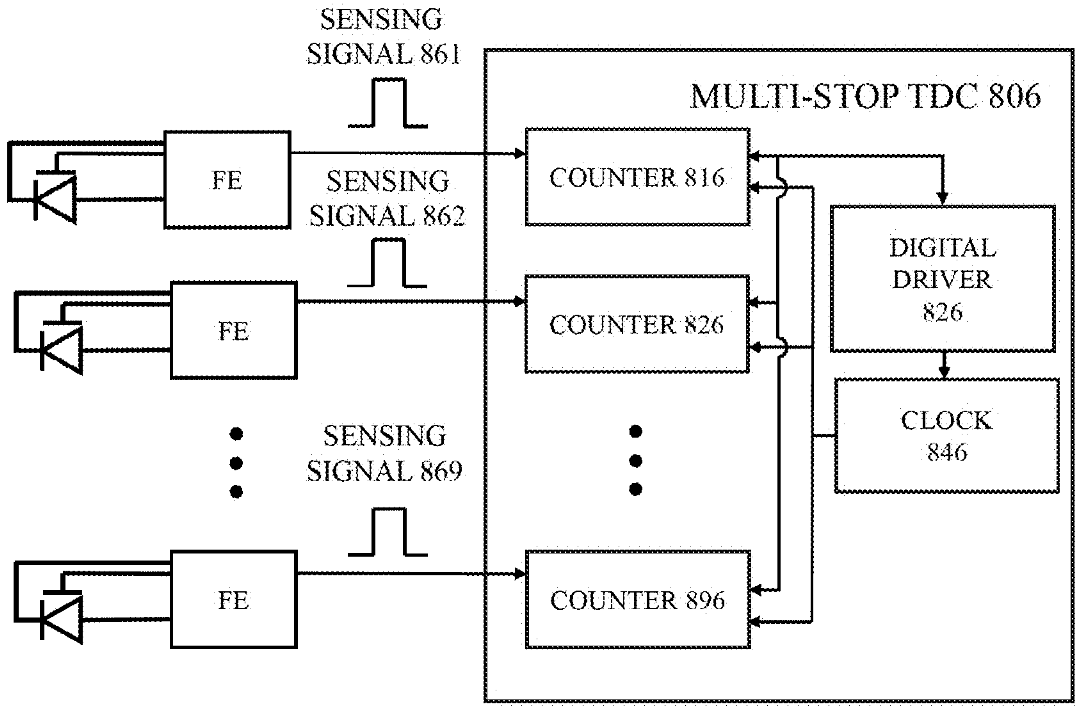
FIG. 8 shows a time-to-digital converter that receives sensing signals from photodetector systems in accordance with an embodiment of the present disclosure.

FIG. 8 shows a multi-stop TDC 806 that includes a plurality of counters including a first counter 816, a second counter 826, and a third counter 896. The multi-stop TDC 806 includes a digital driver 826 and a clock 846 that function similarly to the digital driver 726. Each counter of the multi-stop 806 receives a respective sensing signal. The first counter 816 receives a first sensing signal 861 from a first detector coupled to the multi-stop TDC 806. The second counter 826 receives a second sensing signal 862 from a second detector coupled to the multi-stop TDC 806. Each of the remaining counters up to the third counter 896 (which provides a third sensing signal 869 to the third counter 896) likewise provides a respective sensing signal to a counter in the multi-stop TDC. The clock 846 provides a clock signal to each of the counters 816, 826, 896. Each counter provides a triggering time in a similar manner as the counter 716.

Figure 9:
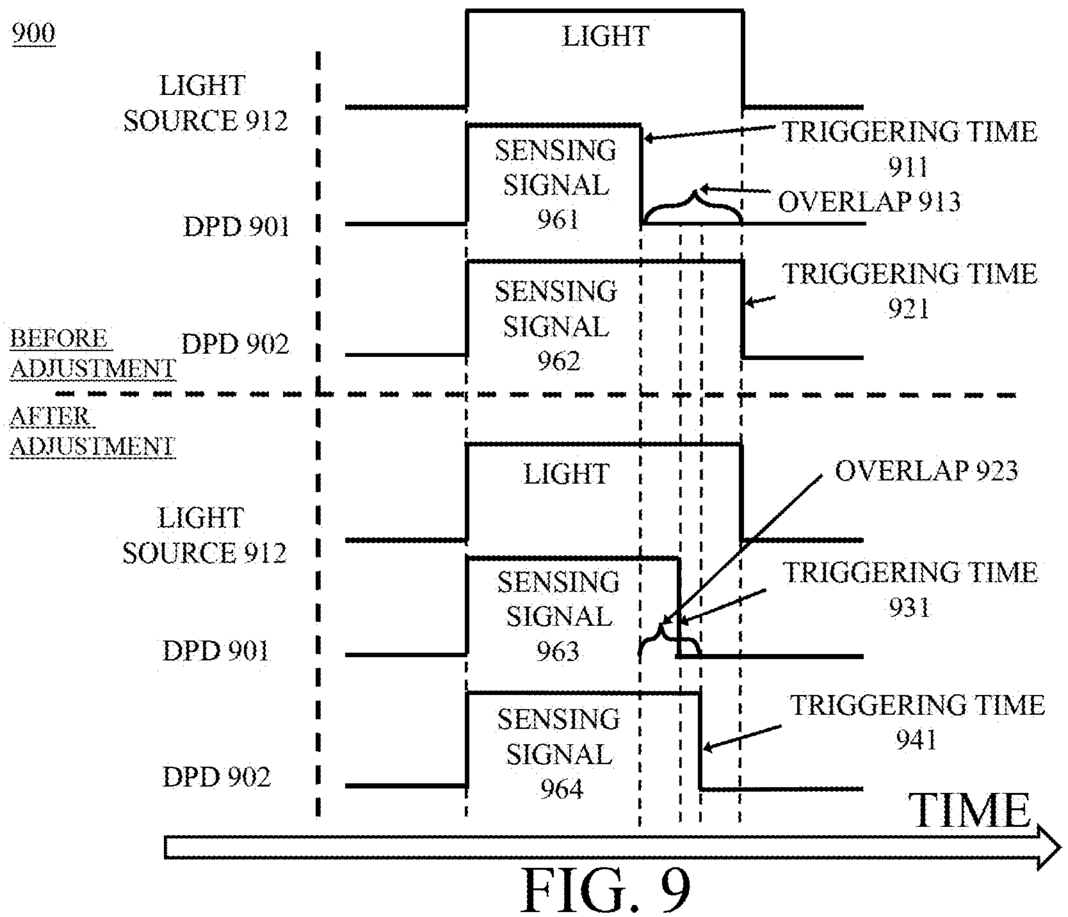
FIG. 9 shows triggering times before and after adjustment in accordance with an embodiment of the present disclosure.

To visually describe the benefits of the embodiments described herein, a timing chart 900 is shown in FIG. 9. The timing chart 900 includes an upper section describing a time period before any DPD is adjusted, where a sensing signal 961 is produced by a first DPD 901 and a sensing signal 962 is produced by a second DPD 902 while a light source 912 is turned on and then off. The sensing signals 961, 962 have an overlap amount 913. The overlap amount 913 is an amount of time between the respective triggering times of the first DPD 901 and the second DPD 902. After adjustment, shown in a lower section of the timing chart 900, the overlap amount 913 is reduced a smaller overlap amount 923. The state of the light source 912 turning on and then off is kept fixed between the upper and lower sections of the timing chart 900 to demonstrate the changes to the triggering times of the sensing signals. In practice, the length of time that the light source 912 is kept on may be reduced before the triggering times of the DPDs are adjusted.

The sensing signal 961 of the first DPD 901 has an associated triggering time 911. The sensing signal 962 of the second DPD 902 has an associated triggering time 921. Without adjusting any parameters (e.g., bias voltage) of a front-end circuit connected to the first DPD 901 or a front-end circuit connected to the second DPD 902, the light source 912 needs to remain on until the last DPD triggers (in this example, when the second DPD 902 triggers at the triggering time 921). Thus, the light source continues to draw power after some DPDs, such as the first DPD 901, have already triggered. With adjustment techniques, as described herein, there are significant improvements.

To reduce the amount of time that the light source 912 stays on (and therefore consume less power), a critical charge threshold of the first DPD 901 and a critical charge threshold of the second DPD 902 are adjusted by a bias signal for each of the DPDs. In some embodiments, one or more charge thresholds is unchanged independently. In one example, the triggering time 921 of the second DPD 902 is lowered while the triggering time 911 of the first DPD 901 remains the same. Altering the threshold of one DPD may not affect the performance of any other DPD, thereby enabling greater control without introducing noise.

One or more processors (e.g., control circuitry 408) receive the triggering time 911 of the first DPD 901 and the triggering time of the second DPD 902 and determine a suitable bias signal to achieve a desired change in triggering time. For example, a charge threshold may be increased to lengthen a triggering time or decreased to shorten a triggering time.

One or more processors may adjust a bias signal (e.g., bias voltage) of the first DPD 901 to alter its triggering time 911. In one example, the adjustment includes sending the bias signal to the front end of a detector including the DPD 901 to increase its triggering time to a triggering time 931 of the sensing signal 963 produced by the first DPD 901 after adjustment. Similarly, the one or more processors adjust the second DPD 902 by sending another bias signal to the front end of a detector including the DPD 902 to decrease its triggering time to the triggering time 941 of the sensing signal 964 produced by the second DPD 902 after the adjustment. The result of this adjustment is that the amount of overlap 913 is reduced to the overlap amount 923 between the sensing signal 963 and the sensing signal 964. Put another way, the triggering time of each DPD is brought closer together.

In cases of multiple sensors, triggering time can vary due to the different positions of the sensors relative to each other. In this case, the light will be "on" when some detectors are already triggered. So, power consumption will not be optimal. Control algorithms can decide to drop measurement after some time delay, or the sensitivity of the sensors can be adjusted to make the triggering times similar, or both can be combined. It is also possible to restart measurement with the detector which is triggered fastest.

At this point it should be noted that techniques for time-based measurements using dynamic photodetectors in accordance with the present disclosure as described above may involve the processing of input data and the generation of output data to some extent. This input data processing and output data generation may be implemented in hardware or software. For example, specific electronic components may be employed in one or more processors, a dedicated circuit or similar or related circuitry for implementing the functions associated with measuring physiological parameters with photodetectors, implementing health data processing algorithms and photodetector control algorithms, implementing neural networks, performing event detection, and so forth in accordance with the present disclosure as described above. Alternatively, one or more processors operating in accordance with instructions may implement the functions associated with neural networks, controllers, algorithms, or other processes in accordance with the present disclosure as described above. If such is the case, it is within the scope of the present disclosure that such instructions may be stored on one or more non-transitory processor readable storage media (e.g., a magnetic disk, SSD or other storage medium), or transmitted to one or more processors via one or more signals embodied in one or more carrier waves.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

The invention claimed is:

1. A system for determining a physiological parameter, the system comprising:

one or more photodetector systems configured to receive light from a light source, wherein the one or more photodetector systems comprises a front-end circuit and a photodetector, wherein the photodetector comprises an anode and a cathode;

a plurality of switches coupled to the anode and the cathode; and time-to-digital converter circuitry configured to receive a sensing signal from the front-end circuit and output a triggering time for determining the physiological parameter;

wherein the one or more photodetector systems are further configured to produce the sensing signal by operating the plurality of switches to apply a forward bias voltage across the anode and the cathode.

2. The system of claim 1, wherein the one or more photodetector systems are further configured to produce the sensing signal by operating one of the plurality of switches to produce the sensing signal by providing an impedance to the anode, wherein the sensing signal is produced until the impedance transitions to a voltage drop on the anode.

3. The system of claim 1, wherein the photodetector comprises a gate, the plurality of switches is coupled to the anode, the cathode and the gate, wherein one or more control signals implement a reset mode of operation of the front-end circuit, a load mode of operation of the front-end circuit, and a sense mode of operation of the front-end circuit, wherein the instructions, when executed by the one or more processors, cause the system to:

put the front-end circuit in the reset mode of operation by connecting the anode to ground, connecting the gate to ground, and applying a reverse bias voltage across the cathode and the anode;

put the front-end circuit in the load mode of operation by providing a voltage to the anode; and put the front-end circuit in the sense mode by maintaining the anode in a floating state and applying the forward bias voltage across the cathode and the anode.

4. The system of claim 1, further comprising:

one or more processors; and memory storing instructions that, when executed by the one or more processors, cause the system to:

generate a bias signal based on the triggering time;

apply the bias signal to the front-end circuit to increase an amount of overlap in time between the sensing signal and another sensing signal of the one or more photodetector systems; and determine the physiological parameter responsive to applying the bias signal.

5. The system of claim 4, wherein the instructions, when executed by the one or more processors, cause the system to apply the bias signal to the front-end circuit to increase the amount of overlap by adjusting an accumulated charge threshold of the photodetector.

6. The system of claim 4, further comprising a plurality of photodetector systems including the one or more photodetector systems, wherein the plurality of photodetector systems and the time-to-digital converter circuitry are included in a group, wherein the system further comprises a plurality of copies of the group, and wherein the instructions, when executed by the one or more processors, cause the system to:

determine the physiological parameter based on at least one sensing signal from each of the plurality of copies of the group.

7. The system of claim 1, wherein the time-to-digital converter circuitry comprises at least one counter configured to receive the sensing signal and output the triggering time of the sensing signal.

8. The system of claim 7, wherein the at least one counter comprises a plurality of counters connected in series with the front-end circuit of each of the one or more photodetector systems.

9. The system of claim 7, wherein the at least one counter comprises a plurality of counters connected in parallel to the front-end circuit of each of the one or more photodetector systems.

10. A method of controlling one or more photodetector systems to determine a physiological parameter, the method comprising the steps of:

receiving light provided by a light source at the one or more photodetector systems, wherein the one or more photodetector systems comprises a front-end circuit and a photodetector that receives the light, wherein photodetector comprises an anode and a cathode, and wherein a plurality of switches is coupled to the anode and the cathode;

producing a sensing signal from the front-end circuit based on the photodetector receiving the light by operating the plurality of switches to apply a forward bias voltage across the anode and the cathode; and receiving the sensing signal by time-to-digital converter circuitry that outputs a triggering time for determining the physiological parameter.

11. The method of claim 10, wherein the sensing signal is produced by providing an impedance to the anode, wherein the sensing signal is produced until the impedance transitions to a voltage drop on the anode.

12. The method of claim 10, wherein the photodetector comprises a gate, the plurality of switches is coupled to the anode, the cathode and the gate, the method further comprising:

putting the front-end circuit in a reset mode of operation by connecting the anode to ground, connecting the gate to ground, and applying a reverse bias voltage across the cathode and the anode;

putting the front-end circuit in a load mode of operation by providing a voltage to the anode; and putting the front-end circuit in a sense mode by maintaining the anode in a floating state and applying the forward bias voltage across the cathode and the anode.

13. The method of claim 10, further comprising:

generating a bias signal based on the triggering time;

applying the bias signal to the front-end circuit to increase an amount of overlap in time between the sensing signal and another sensing signal of the one or more photodetector systems; and determining the physiological parameter responsive to applying the bias signal.

14. The method of claim 13, wherein applying the bias signal comprises applying the bias signal to the front-end circuit to increase the amount of overlap by adjusting an accumulated charge threshold of the photodetector.

15. The method of claim 10, further comprising providing a plurality of photodetector systems as a group including the one or more photodetector systems and the time-to-digital converter circuitry, providing a plurality of copies of the group, and the method further comprising:

determining the physiological parameter based on at least one sensing signal from each of the plurality of copies of the group.

16. The method of claim 10, wherein the time-to-digital converter circuitry comprises at least one counter receiving the sensing signal and outputting the triggering time of the sensing signal.

17. A user-worn device for determining a physiological parameter, the user-worn device comprising:

one or more photodetector systems configured to receive light from a light source, wherein the one or more photodetector systems comprises a front-end circuit and a photodetector, wherein the photodetector comprises an anode and a cathode;

a plurality of switches coupled to the anode and the cathode; and time-to-digital converter circuitry configured to receive a sensing signal from the front-end circuit and output a triggering time for determining the physiological parameter;

wherein the one or more photodetector systems are further configured to produce the sensing signal by operating the plurality of switches to apply a forward bias voltage across the anode and the cathode.

18. One or more non-transitory computer-readable media storing executable instructions that, when executed by one or more processors, determine a physiological parameter using one or more photodetector systems, wherein the one or more photodetector systems comprises a front-end circuit and a photodetector, wherein the photodetector comprises an anode and a cathode, and wherein a plurality of switches is coupled to the anode and the cathode, wherein the physiological parameter is determined by:

receiving light provided by a light source at the one or more photodetector systems, wherein the photodetector receives the light;

producing a sensing signal from the front-end circuit based on the photodetector receiving the light by operating the plurality of switches to apply a forward bias voltage across the anode and the cathode; and receiving the sensing signal by time-to-digital converter circuitry that outputs a triggering time for determining the physiological parameter.

* * * * *